(12) United States Patent  
Belkin

(10) Patent No.: US 8,499,374 B2
(45) Date of Patent: Aug. 6, 2013

(54) METHOD AND SYSTEM FOR THE THERAPEUTIC APPLICATION OF DRY CARBON DIOXIDE GAS

(76) Inventor: Sam Belkin, San Diego, CA (US)

(*) Notice: Subject to any disclaimer, the term of this patent is extended or adjusted under 35 U.S.C. 154(b) by 392 days.

(21) Appl. No.: 12/953,315

(22) Filed: Nov. 23, 2010

(65) Prior Publication Data

US 2011/0125083 A1  May 26, 2011

Related U.S. Application Data

(60) Provisional application No. 61/283,033, filed on Nov. 25, 2009.

(51) Int. Cl.
*A61H 33/06* (2006.01)
(52) U.S. Cl.
USPC ............................................................. 4/524
(58) Field of Classification Search
USPC ................................................ 4/524, 528, 531
See application file for complete search history.

(56) References Cited

U.S. PATENT DOCUMENTS

| 3,772,713 | A | * | 11/1973 | Roullier | 4/524 |
| 4,044,772 | A | * | 8/1977 | Schloss | 607/87 |
| 2009/0019634 | A1 | * | 1/2009 | Lipponen | 4/524 |
| 2011/0209283 | A1 | * | 9/2011 | Chen | 4/524 |

* cited by examiner

*Primary Examiner* — Huyen Le
(74) *Attorney, Agent, or Firm* — Eric A. Hanscom; Todd J. Langford

(57) ABSTRACT

A sealable cabinet that permits a human or animal to experience a dry bath for carbon dioxide or other gases, with said cabinet fitted with gas, water, and power connections, and a controller to optimize the temperature, gas concentrations, and water vapor content of the interior, plus a switchable means for selecting between a sauna environment and said carbon dioxide bath, with a business method that enables a provider of services involving such equipment to achieve a profitable interface with patients and customers.

1 Claim, 5 Drawing Sheets

System configuration

System configuration

Block diagram

Human-Machine Interface

System in use

Control connections

METHOD AND SYSTEM FOR THE THERAPEUTIC APPLICATION OF DRY CARBON DIOXIDE GAS

CROSS REFERENCE TO RELATED APPLICATIONS

The present application claims the benefit of priority of U.S. Provisional Application Patent No. 61/283,033 filed Nov. 25, 2009 for Sam Belkin, the entire content of which is incorporated herein by reference.

FEDERALLY SPONSORED RESEARCH AND DEVELOPMENT

Not applicable

BACKGROUND OF THE INVENTION

1. Field of the Invention

The present invention relates generally to the several fields that support wellness of both humans and animals, and particularly to the use of dry carbonic baths to achieve such wellness.

2. Description of the Prior Art

Many methodologies exist by which beneficial effects in living tissue result from the application of dry carbon dioxide gas, carbon dioxide dissolved in water, and similar methods that stimulate the transcutaneous passage of carbon dioxide molecules into living tissues. European literature describes substantial benefits from such therapy, including reduction of blood pressure, improved vascularization, and subjectively-perceived and reported higher energy levels.

In the marketplace there appear various primitive means by which a body is mostly submerged in water with a high concentration of dissolved $CO_2$, but such processes are uncontrolled and only coincidentally are key parameters optimized. Conventional baths in water with a high concentration of $CO_2$ are difficult to standardize, and often results cannot be replicated.

Market research has also identified various cabinets of fabric, plastic, wood, or metal that permit the application of dry gases including $CO_2$, but such processes are also uncontrolled and in a given session are only coincidentally optimized.

The present invention is a clear departure from prior art, as it optimizes the process of exposing the living body to gaseous $CO_2$, automates aspects of said exposure, and thereby maximizes benefits from transcutaneous absorption of $CO_2$ by living tissue of humans and animals. The present invention is also differentiated from prior art by its means of deployment into the marketplace.

Prior art methods and devices exist for applying $CO_2$ in gaseous form, or as a solute dissolved in water, but they do not provide an optimized combination of gases, temperature, humidity, and exposure time, which when balanced properly are critical to the efficiency of the process and the results it obtains.

Prior art methods and equipment for applying $CO_2$ in gaseous form, or dissolved in water, fail to provide automated management of those parameters to permit maximum results.

Patent number RU 2066548 Class A 61 H 33/06 by inventor SAM BELKIN with priority date of Jul. 16, 1992 discloses a system that is similar to the present invention and is by the same inventor. However, the present invention is differentiated from the inventor's previous invention by the following:

a. The previous invention provided approximate gas and temperature levels, while the present invention benefits from studies by the inventor that discovered optimum gas and temperature levels for specific situations, and uses a micro-processor or microcontroller and closed-loop systems to ensure operation at those levels, thus increasing the probability of achieving predictable and repeatable results.

b. The previous invention used adjustments that set crude levels of gas concentrations and temperatures. The present invention uses methods to maintain precise levels of gas concentrations and temperatures that can be adjusted by the operator to meet changing circumstances or the needs of the patient or client.

c. The previous invention used a simple fan to provide air flow in the cabinet. The present invention uses a precise fan, mixing system, and ducting arrangement to ensure homogeneity of the gases in the cabinet, optimizing the nature of the gas-skin interface at all points on the body of the patient or client.

In the prior art are enclosures that provide the user with combinations of humidity and temperature, as a personal or single-user sauna. This is known and accepted technology. The present invention is intended to include combination cabinets that enable the selection of either a dry carbonic bath or a conventional sauna. Though the sauna alone is not considered to be inventive, the combination of sauna plus dry $CO_2$ bath is.

Various commercial products and methods such as "Rio-Blush," "Carbossi," and organizations employing the Italy-based procedure given the generic name "carbossiterapia" use needles to inject $CO_2$ under the skin. In the west, the procedure has been given the name "carboxytherapy," and is intended to improve skin tone and remove wrinkles. In such instances, the procedure involves the use of fine needles to inject $CO_2$ under the skin.

Sanatorii in Belarus, Tamas Bender MD in Hungary, the Włókniarz Sanatorium in Busko-zdrój, Poland, Reabox in Russia, and other (mostly Eastern European) spas and medical centers make and/or use carbon dioxide dry and wet bath systems of various sorts, but the results they achieve are not as beneficial as they could be if the operational parameters were controlled as they are in the case of the present invention.

Existing systems also fail to exploit the physical similarity between the $CO_2$ bath cabinet and the cabinet required by a personal sauna, while the present invention includes the possibility of a single product that offers the selection of either function.

Existing systems do not provide commercial optimization, permitting the use of credit/debit cards and transaction efficiency.

The present invention does not use needles, and does employ unique monitoring and control technologies to ensure optimization of the temperature, $CO_2$ concentration, and water vapor concentration to precisely manage the passage of $CO_2$ through the skin of the user.

The present invention does permit the cabinet to be used either as a dry $CO_2$ bath or as a sauna.

The present invention does include the employment of credit/debit card devices to improve transaction efficiency.

In these respects, the present invention substantially departs from the concepts and designs of prior art. In so doing, the present invention improves the mechanisms and processes by which dry carbon dioxide gas is applied to living tissue, facilitates transcutaneous absorption of the gas by living tissue, provides unique opportunities to therapy-oriented businesses that adopt the CO2 bath equipment and procedure, reduces the skill level requirements for technicians using the technology, improves measurable beneficial results, elevates customer/User satisfaction, and permits a unique combination of dry CO2 bath and sauna in a personal or single-occupant cabinet.

OBJECTIVES OF THE INVENTION

In view of the foregoing disadvantages inherent in the known methods and practices for the application of carbon dioxide to living tissue, of both humans and animals, the present invention provides functionality and effectiveness not available from existing systems and methods.

The overall objective of the present invention is to provide a cost-effective, safe, and effective cabinet in which the human or animal can be enclosed, and automated mechanisms by which the parameters of relative gas concentrations, temperature, water/humidity, and time are managed.

Another objective of the present invention is to provide a system that controls all parameters of the process, thus enabling consistent and repeatable results.

Another objective is to control dew point inside the cabinet, managing condensation on the skin and optimizing penetration of the skin by the high ambient carbon dioxide concentration.

Another objective is to provide wellness, allopathic medical, chiropractic, veterinary, and other health practices with an optimized, safe, simple, reliable, low cost, and profitable method for the application of dry CO2 gas to the skin, causing transcutaneous absorption.

Another objective is to provide a system that can be adapted to use other gas combinations and concentrations, temperature profiles, humidity conditions, and time periods to continually update the procedure in software or firmware, with minimal hardware changes.

Other objects and advantages of the present invention will become evident to the reader. It is intended that all systems fall within its scope if they (1) enable a healthcare facility to provide dry carbonic baths to Users, (2) utilize a cabinet or flexible fabric or plastic cabinet to house the User/client during such exposure, (3) automate all or part of the control of operational parameters of said CO2 exposure, (4) combine a personal sauna with a dry CO2 bath, and (5) provide the facility with a method and means for efficiently managing transactions, thus supporting the conduct of business with said equipment and technology.

To the accomplishment of the above and related objects, this invention may be embodied in the forms illustrated in the accompanying specification and drawings. However, the specification and drawings are illustrative of the basic concepts only; there are many possible configurations and derivatives lying within the intended scope of the invention.

BRIEF SUMMARY OF THE INVENTION

The present invention can be executed as an enclosure in which a User (whether human or animal) can sit or stand with head exposed to ambient air. Hereafter, the term "cabinet" shall be used whether it refers to a hard cabinet, a soft fabric with a rigid frame, or a flexible plastic enclosure.

A flexible seal creates a barrier between the User's neck and the edge of an appropriately-positioned aperture for the User's head. That seal attaches to the cabinet's edge or surface and circumscribes the User's neck, effectively preventing gas passage from the cabinet to the ambient atmosphere.

A CO2 source—either a generator (known technology using methane combustion, etc.), a CO2 tank, or a central gas source serving multiple locations—is attached to the cabinet, and its content is metered into the cabinet by a valve opened or closed by a control circuit. Using a flowmeter, the system can inject a known amount of CO2 with the assumption that the desired concentration will be approximated (since internal volume of the cabinet is established), or can inject CO2 and use gas concentration measurement methods to provide a signal to the control system to permit closed-loop management to meet therapeutic goals. A specific CO2 concentration level up to 60% can be established and maintained, which compares to the CO2 concentration in normal atmosphere of about 0.04%.

A water source is attached to the cabinet, and its content is added by means of a well-known humidification apparatus. Humidity is monitored, and provides a signal to the control system to permit management to achieve a gaseous moisture concentration of about 95%.

A heater is included in the cabinet, or placed in the air path, to permit optimization of the temperature of the gas mixture within.

A temperature sensor is used to generate a signal to the control system to permit management of internal temperature at a point between 90 and 105 degrees Fahrenheit.

The cabinet is equipped with an internal seat or platform for the convenience of the User, and said seat can be adjusted for height to accommodate various Users. The seating surface is made porous or of an open-weave fabric, thus exposing more of the user's skin to the internal gases.

The cabinet is equipped with an air duct that permits the internal combination of gases to flow in a generally circular path from bottom to top or top to bottom, ensuring good distribution and mixing of gases within the cabinet.

The air passage channel is equipped with a fan or blower to cause blending and circuitous air movement with sufficient turbulence to ensure homogeneity of the internal gas mixture.

The overall system is equipped with a timers to permit control of the length of the steps comprising the procedure.

The overall system is equipped with a safety circuit to detect potentially dangerous conditions and failures, and to automatically shut down the processes if a fault is detected. Detection of a fault causes the safety circuitry to close all valves, turn off the heater and blower, and actuate an audible and visible alarm. To the maximum practical extent, said safety circuitry is independent of the basic controller circuit.

A microcontroller, microprocessor, or computer is used to manage all processes and automate them, thus permitting operational changes to be introduced via software.

The controller circuit provides a human interface, such as a keypad and display, at a convenient location on the cabinet.

The present invention also includes a combination cabinet capable of allowing the user or practitioner to select either a personal sauna environment or a dry CO2 bath.

The present invention also includes methods by which the dry CO2 bath is profitably made available to the public. It can be purchased or leased by a healthcare or wellness practitioner or by a user, or installed at a healthcare or wellness facility and operated on a per-use basis using credit cards or other accounting/payment/tracking methods.

Once the fundamental concepts of the present invention are understood, variations and derivatives will come to mind. The present invention is intended to include those which create a dry CO2 bath optimized for temperature, gas concentrations, humidity, and time, and that optimizes and automates the process. The dry CO2 bath can be integrated into a sauna cabinet, and the user can select between the two functions.

The present invention is also intended to include specific business methods by which the mechanism and process of the present invention interface with the user's payment capabilities.

DESCRIPTION OF THE PREFERRED EMBODIMENT

In the preferred embodiment, the present invention is a rigid cabinet with a door that opens sufficiently to enable the User to enter the cabinet.

The door of the cabinet is hinged, and pivots laterally.

A seat or platform is provided within the cabinet to help position the User.

Sources of carbon dioxide gas and water vapor, and sensors, are provided to an electronic controller circuit that optimizes the gas balance inside the cabinet and controls overall operation.

A heating system is provided, and a temperature sensor is connected to the electronic controller to permit optimization of temperature.

A timer is integrated into the controller to enable control of the time the user is exposed to the dry carbonic bath.

Ducting and a fan circulate the interior gases inside the cabinet, ensuring mixing.

The controller circuit has inputs for temperature, gas concentration, humidity, and a time reference, and uses known logic and simple software to optimize the dry carbonic bath process.

A safety system monitors CO2 concentration, temperature, and time, and faults to an OFF condition with all valves closed and an audible and light alarm when a failure is detected.

The preferred business method enables a practitioner to purchase the present invention and offer its benefits to Users, who will pay for time in the cabinet. However, there are equally preferential methods by which operation of the cabinet is dependent upon acceptance of a Near Field Communication (NFC) portable RF device, or a credit card entered by either the practitioner (thus providing metered operation) or the User.

VARIATIONS UPON THE PREFERRED EMBODIMENT

The enclosure can be rigid (metal, plastic, wood) or flexible, and in the latter case it can be fabric or plastic supported by an internal or external frame.

The cabinet can be attached to free-standing external water and CO2 sources, or such sources can be carried upon a shelf on the rear of the cabinet, so when fitted with wheels the complete system can be rolled from one location to another.

In a hospital or large therapy facility, each cabinet can be part of a group, all of which are attached to central supplies of water, gas, and power.

The cabinet can be sized to seat only one User, or can be sized to seat more than one User.

The cabinet door can be hinged at the bottom, at one side, or at both sides with a central seam, to facilitate entry and exit.

The front door can be fitted with a movement rate controller or damper, to prevent human injury if it inadvertently swings closed upon a portion of the User's body.

The front door of the cabinet can be removable and replaced with a flexible fabric or plastic curtain that is sealed around the edge of the door, thus increasing the internal volume of the cabinet and permitting it to be used with an obese User.

The seating surface can be height-adjustable, or an optional cushion provided to elevate the User's head to match the aperture at the top of the cabinet.

The seating surface, including the backrest, can be fabricated of webbing, thus increasing the area of the user's body that is exposed to the internal gases of the cabinet.

The configuration of the basic cabinet will permit the User to sit upon a chair; a horizontally-elongated cabinet can permit the User to lie on a platform set at a sufficient slant to ensure that the User's head remains higher than the rest of the body, and a vertically-elongated cabinet can permit the User to stand within it.

The collar around the User's neck can be of gas-impervious plastic or fabric, designed to provide a seal between the cabinet's aperture and the neck of the User.

The CO2 management system can inject gas into the known approximate volume of the cabinet to achieve the required concentration when the system is activated, or a gas concentration detection method can be used to permit active management of concentration with feedback to the controller, which then activates a valve. It is superior to enable active management, since the volume of the User is not predictable and a large User will have a higher concentration of CO2, and a small one will have a lower concentration.

An aromatic or therapeutic additive can be combined with the circulating gas.

The circulating air passage provided by the ducting and fan(s) or blower(s) can be achieved outside of the cabinet, as opposed to integrated with the chair. This requires an external duct connecting the bottom of the chamber to the top, with a fan or blower serial to the duct, thus achieving the desired flow rate and homogeneity of the gas-air mixture.

The safety circuit can activate an exhaust fan or blower to remove the gas mixture from the cabinet.

It is not mandatory to individually and manually control all operating parameters. The Human-Machine Interface can include simplified SETTINGS buttons, each of which establish a known combination of operating parameters including time, humidity, gas concentration, and temperature. SETTING "A" might be a substantially different combination than SETTING "B", "C" "D", etc.

The system can be owned or leased by the practitioner or User, who then is responsible for servicing the system (replacing gas tank, etc.). Alternatively, credit card processing equipment with communication can be integrated into the system, so individual treatments or groups of treatments can be purchased by either the practitioner or a User, thus enabling another party to actually own the system.

DETAILED DESCRIPTION OF THE INVENTION

Step-by-step, the present invention is as follows.

The Patient (in a medical setting) or Client (in other settings) (collectively, the "User") is briefed and given a location in which to disrobe, and to don a gas-permeable disposable garment. While changing, the system is powered, seat height is adjusted, and settings are entered for the session. The door is opened, the air dam or collar, which creates a seal between the User's neck and the upper aperture of the cabinet, is fitted around the neck, and the User sits inside. At the end of the session the system is turned off, the User exits and is offered a shower. The Patient/Client dresses and leaves.

Figure 1:
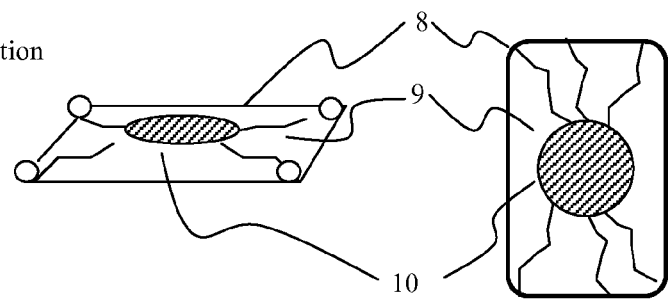
FIG. 1 is a schematic side view of the system according to selected embodiments of the current disclosure.
Figure 1:
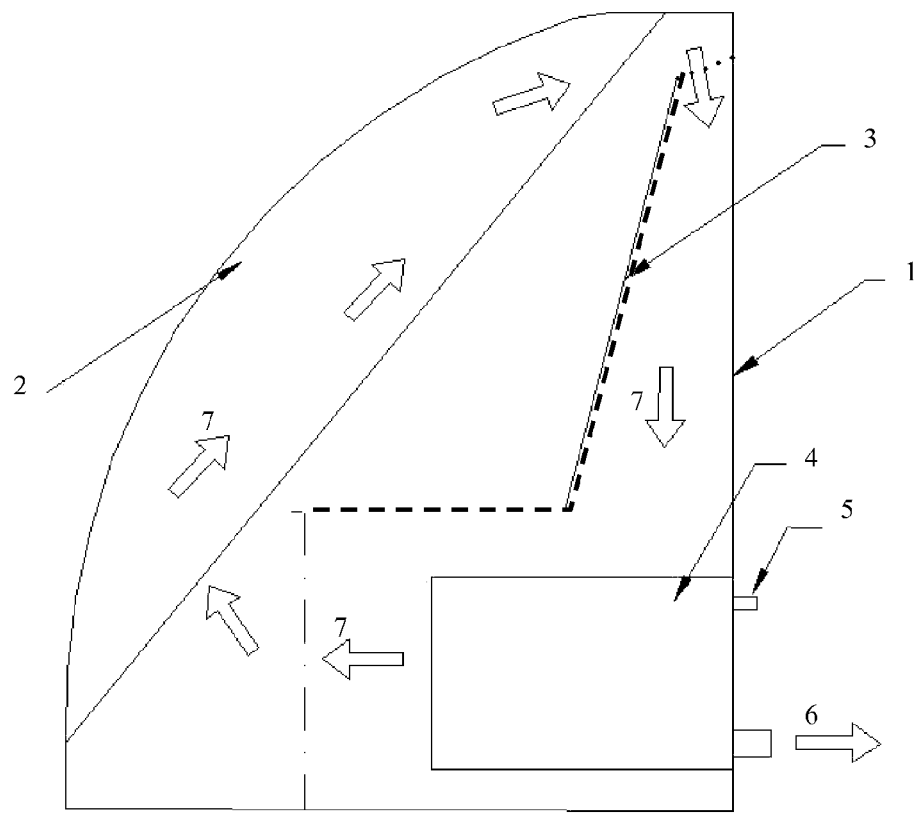

FIG. 1 depicts a side view and partial top view of the system, in which the cabinet or cabinet 1 is fitted with a hinged or removable door 2 and a perforated internal seat and seatback 3 under which is a combined gas management system and blower 4 into which $CO_2$ and water vapor flow from an external source via port 5 and excessive internal pressure can be vented via outlet 6, while the blower 4 causes airflow 7 within the cabinet, atop which is an large opening 8 with an air dam 9 to prevent gas leakage around the neck of the User, and an aperture 10 for the head of the User.

Figure 2:
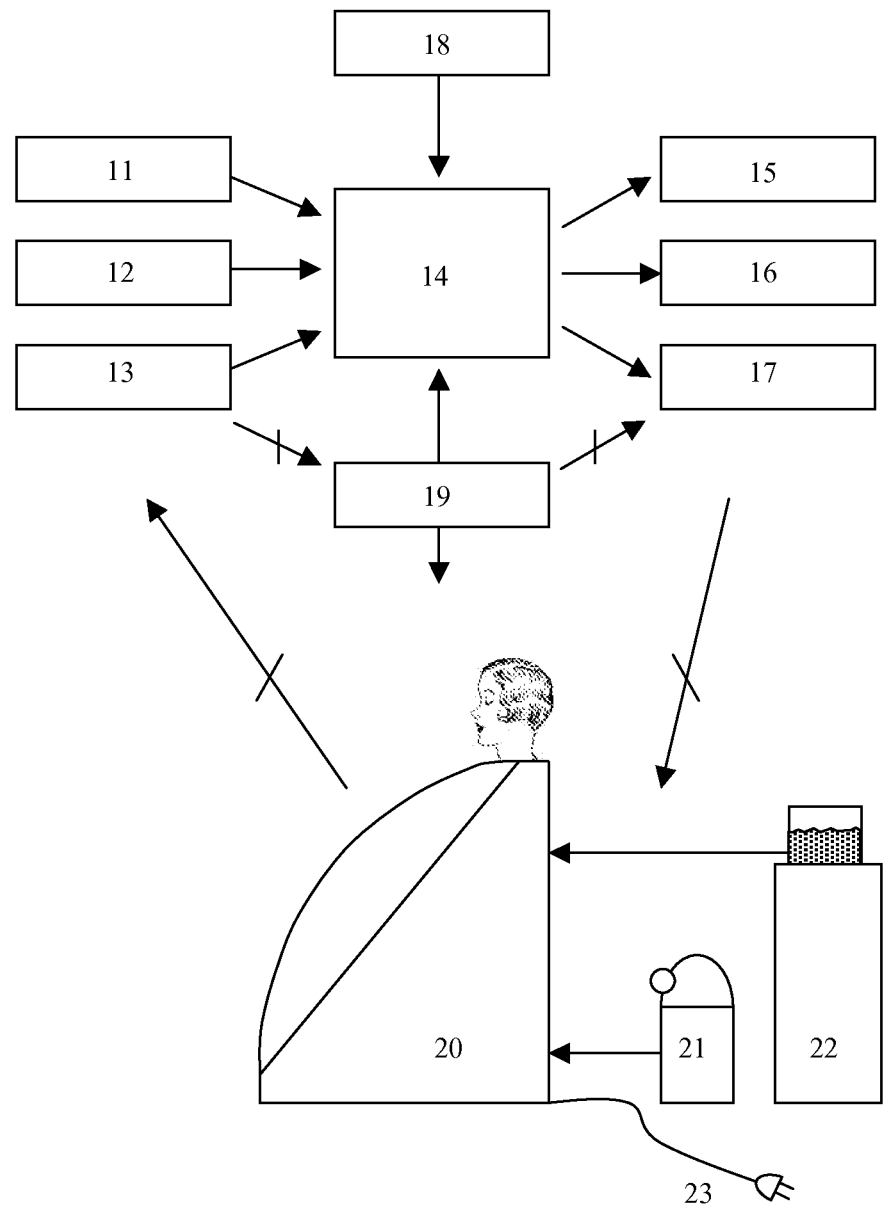
FIG. 2 is a block diagram of control circuitry according to selected embodiments of the current disclosure.

FIG. 2 depicts a block diagram of the control circuitry, in which a gas concentration and flow sensing circuit 11, a temperature sensors circuit 12, and a humidity and dew point detector 13 output their sensed values to a central processor or microcontroller 14, which regulates gas valves for $CO_2$ and other gases 15, heater 16, and humidifier 17, plus a settable timer 18 to control the period of system operation and a safety system 19 to reduce hazard, which monitors operating conditions and can exercise independent control over the $CO_2$ gas valve 15, heater, 16, and humidifier 17, all to regulate the overall conditions in the cabinet system 20 by controlling gas 21, moisture content of the air from a water source 22, and power 23.

Figure 3:
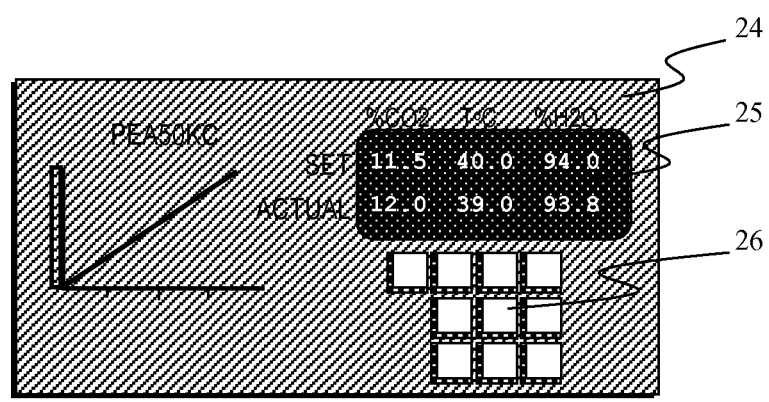
FIG. 3 shows a user interface according to selected embodiments of the current disclosure.

FIG. 3 depicts the human-machine interface, a control panel 24 that provides visual indications of various parameters 25 and control via a manual entry device such as a keypad 26, whereupon the desired time, temperature, and concentrations of water vapor and $CO_2$ can be set.

Figure 4:
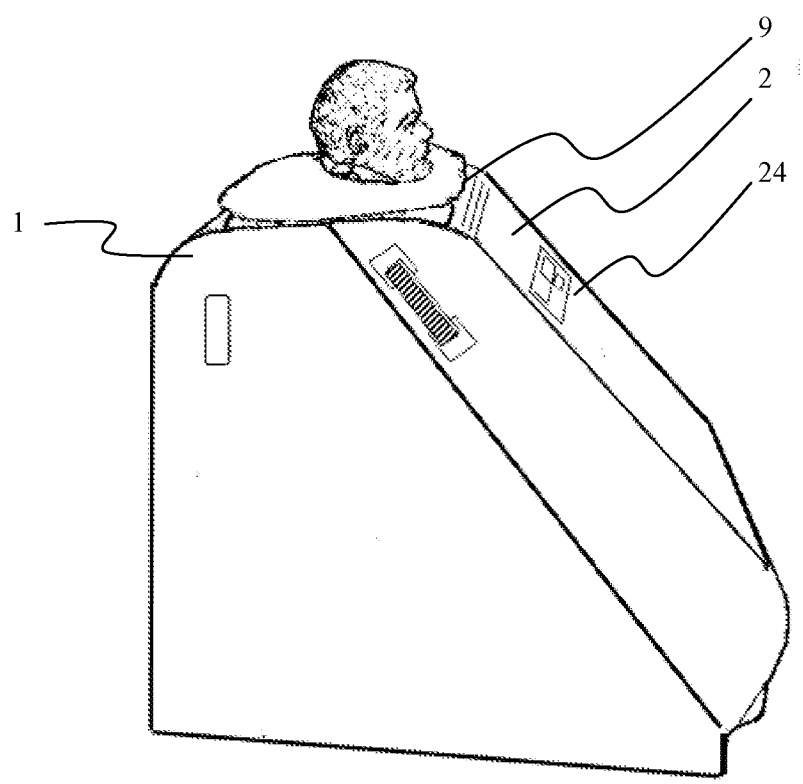
FIG. 4 is a perspective view of the system in operation according to selected embodiments of the current disclosure.

FIG. 4 provides an image of the complete system in operation, where cabinet 1 has an upper opening 9 for the User's head, and is fitted with door 2 on which appears the human-machine interface 24.

Figure 5:
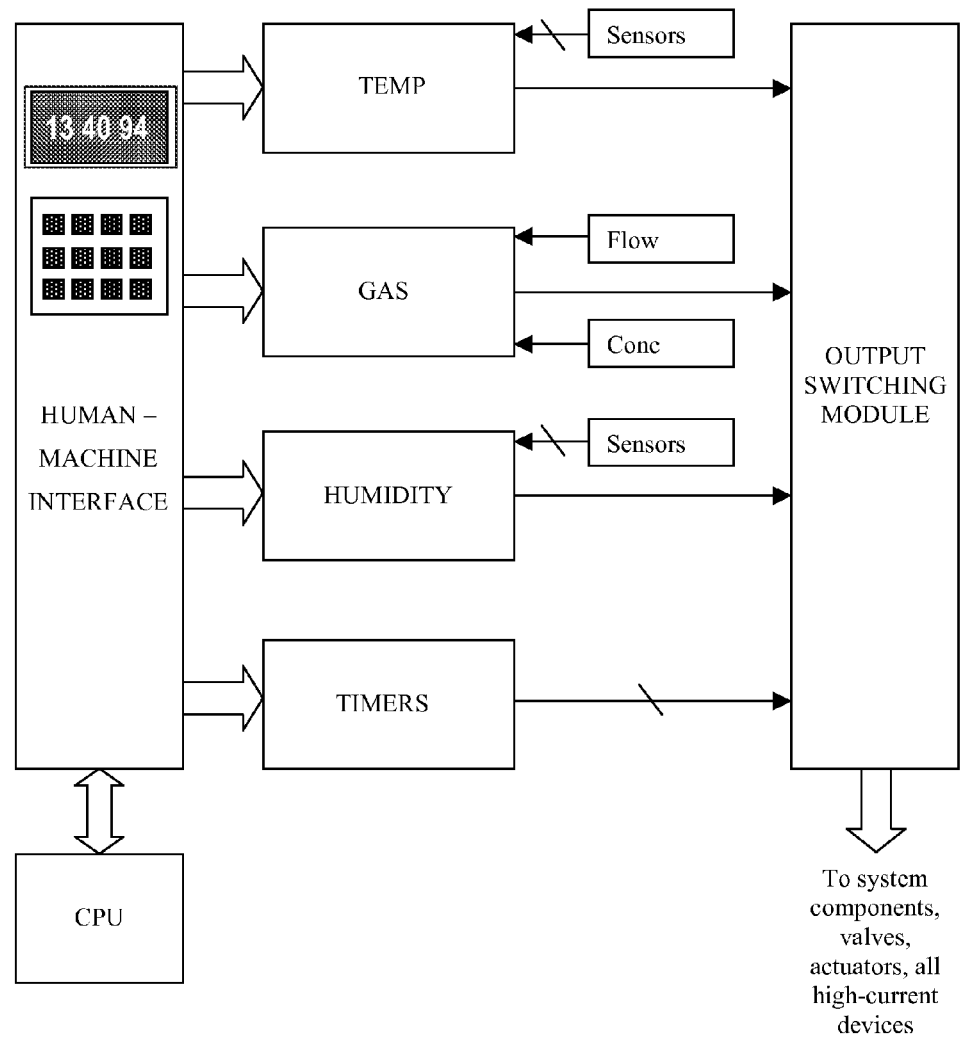
FIG. 5 is a block diagram of control and sensor connections and data flow according to selected embodiments of the current disclosure.

FIG. 5 expands the control and sensor connections and shows data flow.

I claim:
1. A system for the therapeutic application of dry carbon dioxide gas comprising:
an enclosure, where the enclosure comprises a door, a seat, and an aperture through which a user's neck may extend therethrough, where the aperture comprises a means of creating a seal between the enclosure and a user's neck, where a gas is contained within the enclosure; a means of circulating the gas contained within the enclosure;
a source of carbon dioxide and a carbon dioxide valve, where the source of carbon dioxide is in fluid connection with the enclosure thereby allowing carbon dioxide to flow into the enclosure, where the carbon dioxide valve regulates the flow of carbon dioxide from the source of carbon dioxide into the enclosure;
a humidifier, where the humidifier is operably connected to the enclosure and regulates moisture added into the enclosure;
a heater, where the heater is operably connected to the enclosure thereby adding heat thereto;
a carbon dioxide concentration sensor, where the carbon dioxide concentration sensor determines the concentration of carbon dioxide of the gas and generates a sensed carbon dioxide concentration value;
a carbon dioxide flow sensor, where the carbon dioxide flow sensor determines the flow rate of carbon dioxide entering the enclosure and generates a sensed carbon dioxide flow value;
a temperature sensor, where the temperature sensor determines the temperature of the air-gas mixture within the enclosure and generates a sensed temperature value;
a humidity sensor, where the humidity sensor determines the humidity of the gas within the enclosure and generates a sensed humidity value;
a timer, where the timer generates on and off values;
a control circuit, where the control circuit controls the carbon dioxide valve, heater, and humidifier, where the control circuit accepts the values from the carbon dioxide concentration sensor, the carbon dioxide flow sensor, the temperature sensor, the humidity sensor, and the timer;
a safety circuit, where the safety circuit, independent of the control circuit, controls the carbon dioxide valve, heater, and humidifier, where the safety circuit, independent of the control circuit, accepts the values from the carbon dioxide concentration sensor, the carbon dioxide flow sensor, the temperature sensor, and the humidity sensor;
whereby a user may be substantially enclosed within the enclosure and subject to an environment wherein the temperature, humidity, and concentration of carbon dioxide are controlled.

* * * * *